United States Patent [19]

Krishnan

[11] Patent Number: 5,264,588
[45] Date of Patent: Nov. 23, 1993

[54] PROCESS FOR PREPARING CHLORO-N-PHENYLPHTHALIMIDE

[75] Inventor: Chandrasekhar Krishnan, Grand Island, N.Y.

[73] Assignee: Occidental Chemical Corporation, Niagara Falls, N.Y.

[21] Appl. No.: 946,137

[22] Filed: Sep. 17, 1992

[51] Int. Cl.$^5$ ............................................. C07D 209/48
[52] U.S. Cl. ................................................... 548/476
[58] Field of Search ......................................... 548/476

[56] References Cited

U.S. PATENT DOCUMENTS 4,116,980  9/1978  Webb ............................ 548/476 X
4,769,493  9/1988  Ito et al. ........................ 548/476 X

OTHER PUBLICATIONS

W. R. Orndorff & D. S. Pratt, American Chemical Journal, vol. 47, p. 89 (1912).
W. Schneider & H. Gotz, Arc. Pharm., vol. 294, p. 506 (1961).

Primary Examiner—Mary C. Lee
Assistant Examiner—Jacqueline Haley
Attorney, Agent, or Firm—Wayne A. Jones; Richard D. Fuerle

[57] ABSTRACT

Disclosed is a method of preparing a chloro-N-phenylphthalimide. A solution is prepared of a chlorophthalic acid or anhydride and aniline in water as the only solvent and the solution is heated to produce the product. The preferred chlorophthalic acid is 3,4,6-trichlorophthalic acid.

20 Claims, No Drawings

PROCESS FOR PREPARING CHLORO-N-PHENYLPHTHALIMIDE

BACKGROUND OF THE INVENTION

This invention relates to a process for reacting a chlorophthalic acid with aniline to produce a chloro N-phenylphthalimide. In particular, it relates to such a process wherein the only solvent is water.

3,4,6-Trichloro-N-phenylphthalimide (TiCNPP) is an intermediate used in the preparation of quinolone antibacterial drugs. Until now, this compound was prepared by reacting 3,4,6-trichlorophthalic acid (TiCPA) with aniline in glacial acetic acid. See "An Expedient Route to the Quinolone Antibacterial Intermediate, 3,4,5-Trifluorobenzoic Acid" by Neil J. O'Reilly et al. Synlett Letters, page 609 (1990). While that method successfully produced TiCNPP, it was not entirely satisfactory because it also produced sodium acetate, which created a waste disposal problem. In addition, the process for producing the TiCPA was performed in water (see U.S. Pat. No. 4,981,999) and the use of glacial acetic acid therefore required isolating the TiCPA from the water before reacting it with the aniline.

Since the process for producing the TiCPA was conducted in water and water is inexpensive, it might seem reasonable to attempt the reaction of that starting material with aniline in water as well. However, for several reasons it was widely believed that the reaction would not occur in water. First, the reaction is reversible and one of the products of the reaction is water, so it was thought that the presence of water would shift the reaction equilibrium toward the starting material. Second, the phenyl group provided by the aniline performs only the function of protecting the diacid groups during subsequent fluorination of the chlorine groups with potassium fluoride. After the fluorination is complete, the phenyl group is removed and the diacid is formed once again. Since the phenyl group is not an essential portion of the product, the reaction was attempted with methyl amine, which would provide a methyl group to protect the diacid groups during fluorination. However, when methyl amine was tried in water, even under a variety of reaction conditions, no product was produced. Since methyl amine is more soluble and more reactive than aniline and did not work in water, it was concluded that the reaction of TiCPA with aniline would not occur in water.

SUMMARY OF THE INVENTION

I have discovered that TiCPA reacts with aniline in 100% water. This reaction occurs even though no co-solvent is present and nothing, not even a surfactant or catalyst, is added. Aside from the reactants and the water, the only other compound that may be present is two equivalents of sodium chloride which resulted when hydrochloric acid was added to the sodium salts of the acid to form the 3,4,6-trichlorophthalic acid. It is remarkable and surprising that this reaction can occur in water alone.

DESCRIPTION OF THE INVENTION

The starting material for the process of this invention is a chlorinated phthalic acid or anhydride which has the general formula

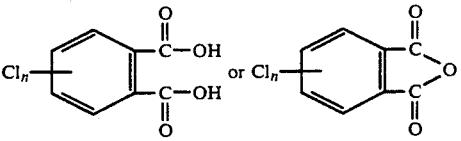

where n equals 1 to 4. Acids are preferred to anhydrides because the previous step produces an acid instead of an anhydride. Particularly preferred is TiCPA, as it is part of a process for producing quinolone intermediates. The TiCPA can be produced by a process described in U.S. Pat. No. 4,981,999, herein incorporated by reference. In that process, tetrachlorophthalic anhydride is reacted with zinc or other hydrodechlorinating metal in the presence of sodium hydroxide or other base.

The chlorinated phthalic acids, their anhydrides, and aniline are all soluble in water and sufficient water is used to dissolve these starting materials. A suitable solid (acid or anhydride) concentration is about 5 to about 50% by weight. The amount of aniline used should be approximately stoichiometric (1 equivalent) with the amount of acid or anhydride when the acid is used, the resultant solution has a pH of about 3 to about 4.

The reaction proceeds when the solution is heated, preferably to reflux (about 95° to about 105° C.) and is normally over in about two to twelve hours. I have found that the reaction can be accelerated if the aniline is added incrementally, in two or more aliquots.

The resulting product, a chloro-N-phenylphthalimide, is insoluble and precipitates from the solution. It can be readily recovered by filtration, washing with water, and drying at about 60° C. under vacuum. The use of the product TiCNPP as a quinolone intermediate is described in hereinabove-cited Synlett article, herein incorporated by reference.

The following examples further illustrate this invention. In these examples, all purity values are by gas chromatograph area %.

EXAMPLE 1

10 g. of 3,4,6-trichlorophthalic acid (98% pure, 0.0364 mol) were placed in a 100 ml three-neck round bottom flask fitted with a water cooled condenser, thermometer, and mechanical agitator. Thereafter, 50 g water (2.78 mol) were added and the mixture heated with stirring to 92° C. Aniline (3.4 g, 0.0366 mol) was added dropwise and the mixture was held at 92° C. for 12 hours. Upon cooling the flask to room temperature, white TiCNPP precipitated out. The precipitate was collected by filtering the product solution followed by washing with a small amount of water. The wet product was then dried at 97° C. in an air circulated oven to obtain 8.8 gm white TiCNPP (93.9% pure; 70% yield).

EXAMPLE 2

This example was similar to Example 1 except that the monosodium salt of TiCPA (TiCPA-MS, 91% pure) which had been reacted with 1 equivalent of HCl was used with 3.0 g aniline. 8.5 g of TiCNPP (73% yield) were obtained.

EXAMPLE 3

TiCPA-MS (95% pure; 40 g, 0.1304 mol) was placed in a 250 ml three-neck round bottom flask fitted with a water cooled condenser, thermometer, and mechanical agitator. Thereafter, 100 g water (5.56 mol) and 13.5 g. concentrated HCl (37% w/w solution; 0.1368 mol)

were added. The mixture was heated gradually with stirring to the reflux point (102° C.) and held there for 2 hours to ensure protonation of TiCPA-MS to TiCPA. At the end of this period the flask was cooled to 95° C. and 12.8 g of aniline (0.1376 mol) were added dropwise. The mixture was further stirred at 95° C. for 9 hours and cooled back to room temperature to obtain a white precipitate of TiCNPP, which was filtered, washed with fresh water, and dried at 1.0 mm Hg and 60° C. to obtain 38.0 g of white TiCNPP (95% pure; 85% yield).

EXAMPLES 4 to 7

Hydrodechlorination (HDC) of tetrachlorophthalic anhydride (TECPAN) to disodium salt of TiCPA (TiCPA-DS)

TECPAN (97% pure; Aldrich Chemical) was placed in a 500 ml three-neck round bottom flask fitted with a water cooled condenser, thermometer, and mechanical agitator. Thereafter 100 g water (5.6 mol) and NaOH were added with stirring and the mixture was heated to 65° C. Zn dust (Zn 65 from Zinc Corp. of America) was added to the flask in 4 equal increments over a 4 hour period. Approximately 4.5 hours after the addition of the first increment of Zn dust, the flask was cooled to room temperature. The Zn salts were filtered off and washed with water to obtain 170 g of a water clear filtrate containing TiCPA-DS. Table 1 gives the results.

Imidization of TiCPA to TiCNPP

The filtrate from the HDC steps was taken in a 500 ml three-neck round bottom flask fitted with a water cooled condenser, thermometer, and mechanical agitator. Thereafter 37.4 g of concentrated HCl (37% w/w solution; 0.3791 mol) were added and the mixture refluxed at 105° C. for 2 hours to ensure protonation of TiCPA-DS to TiCPA. After protonation, the flask was cooled and aniline was added in three equal increments over a 1.5 hour period. Approximately 7 hours after the addition of the first increment of aniline, the flask was cooled back to room 0temperature to obtain a white precipitate of TiCNPP. The precipitate was filtered, washed with water, and dried at 1.0 mm Hg and 60.C to obtain the white TiCNPP product. Table 2 gives the results.

EXAMPLES 8 and 9

TiCPA was heated with methylamine in an attempt to prepare 3,4,6-trichloro-N-methyl phthalimide (TiCNMP). Table 3 gives conditions and the results.

TABLE 1

| Example | TECPAN Amount | Zinc Amount | NaOH Amount | Run Time (h) | HDC Filtrate Amount | TiCPA-DS Yield (%) |
| --- | --- | --- | --- | --- | --- | --- |
| 4 | 40 g | 18.3 g | 18.2 g | 8.0 | 142.5 g | 95.0 |
| 5 | 50 g | 22.9 g | 22.7 g | 7.0 | 164.9 g | 92.0 |
| 6 | 50 g | 22.9 g | 22.0 g | 6.3 | 170.0 g | 91.0 |
| 7 | 40 g | 18.3 g | 18.2 g | 8.3 | 156.8 g | 91.0 |

TABLER 2

| Example | HDC Filtrate Amount | TiCPA in Filtrate | T °C. | Run Time (h) | Aniline Amount | TiCNPP Amount | TiCNPP Yield | TiCNPP Purity |
| --- | --- | --- | --- | --- | --- | --- | --- | --- |
| 4 | 71.3 g | 17.4 g | 98–102 | 5.0 | 6.5 g | 20.2 g | 89.3% | 93.0% |
| 5 | 82.5 g | 21.0 g | 101 | 4.5 | 8.0 g | 22.3 g | 83.0% | 94.8% |
| 6 | 170.0 g | 41.6 g | 102 | 4.5 | 16.3 g | 47.2 g | 85.2% | 91.0% |
| 7 | 156.8 g | 33.3 g | 101 | 7.0 | 13.0 g | 37.1 g | 83.8% | 90.6% |

| Example | TiCPA Amount | Water Amount | CH$_3$NH$_2$ Amount | T °C. | Run Time | TiCNMP Yield |
| --- | --- | --- | --- | --- | --- | --- |
| 8 | 43.4 g | 100.0 g | 5.4 g | 98 | 4.0 | No reaction |
| 9 | 5.0 g | 50.0 g | 5.2 g | 98 | 8.0 | No reaction |

I claim:
1. A method of making a chloro-N-phenylphthalimide comprising
   (A) preparing a composition that comprises
      (1) a chlorophthalic compound having the general formula

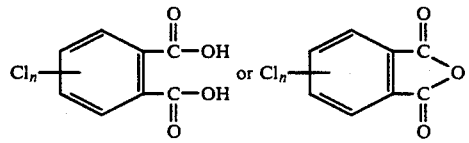

where n is 1 to 4;
      (2) sufficient water to solubilize said chlorophthalic compound wherein said water is the only solvent;
      (3) about a stoichiometric amount of aniline; and
   (B) heating said composition.
2. A method according to claim 1 wherein said composition is heated to reflux.
3. A method according to claim 1 wherein said composition is heated at about 95 to about 105° C.
4. A method according to claim 1 wherein said chlorophthalic compound concentration in said composition is about 5 to about 50 wt. %.
5. A method according to claim 1 wherein said chlorophthalic compound is 3,4,6-trichlorophthalic acid.
6. A method according to claim 5 wherein said composition is prepared by reacting tetrachlorophthalic anhydride with a hydrodechlorinating metal in the presence of a base.
7. A method according to claim 6 wherein said hydrodechlorinating metal is zinc and said base is sodium hydroxide.
8. A method according to claim 1 including the steps of recovering said chloro-N-phenylphthalimide by filtration, washing it with water, and drying it at about 60° C. under vacuum.
9. A method according to claim 8 including the subsequent step of fluorinating said chloro-N-phenylphthalimide with potassium fluoride to produce a fluoro-N-phenylphthalimide.

10. A method according to claim 1 where said aniline is added incrementally to said composition as it is heated.

11. A method of making a chloro-N-phenylphthalimide comprising (A) preparing a composition consisting essentially of
(1) a compound having the general formula

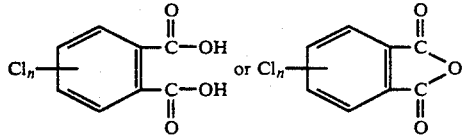

where n is 1 to 4;
(2) as the only solvent, sufficient water to solubilize said compound; and
(3) about a stoichiometric amount of aniline; and (B) heating said composition.

12. A method according to claim 11 wherein said composition is heated at reflux.

13. A method according to claim 11 wherein said position is prepared by reacting tetrachlorophthalic anhydride with a hydrodechlorinating metal in the presence of a base.

14. A method according to claim 11 wherein said chlorophthalic compound is 3,4,6-trichlorophthalic acid.

15. A method according to claim 11 wherein the concentration of said compound in said composition is about 5 to about 50 wt %.

16. A method of making a chloro-N-phenylphthalimide comprising (A) preparing a composition consisting of
(1) a compound having the general formula

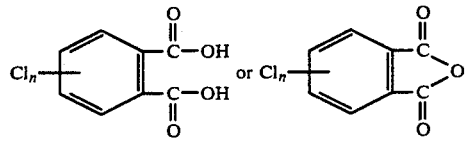

where n is 1 to 4;
(2) sufficient water to solubilize said compound; and
(3) about a stoichiometric amount of aniline; and (B) heating said composition.

17. A method according to claim 16 wherein said composition is heated at reflux.

18. A method according to claim 16 wherein said composition is is prepared by reacting tetrachlorophthalic anhydride with a hydrodechlorinating metal in the presence of a base.

19. A method according to claim 16 wherein said chlorophthalic compound is 3,4,6-trichlorophthalic acid.

20. A method according to, claim 16 wherein the concentration of said compound in said composition is about 5 to about 50 wt %.

* * * * *